United States Patent
Sipiorski

(10) Patent No.: US 8,605,861 B2
(45) Date of Patent: Dec. 10, 2013

(54) SYSTEM FOR MEDICAL IMAGE DISPLAY AND IMAGE FILTER SELECTION

(75) Inventor: Ronald S. Sipiorski, Carpentersville, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 726 days.

(21) Appl. No.: 12/759,723

(22) Filed: Apr. 14, 2010

(65) Prior Publication Data

US 2010/0310049 A1 Dec. 9, 2010

Related U.S. Application Data

(60) Provisional application No. 61/184,354, filed on Jun. 5, 2009.

(51) Int. Cl.
   *H05G 1/64* (2006.01)
(52) U.S. Cl.
   USPC ......................... 378/98.7; 382/132
(58) Field of Classification Search
   None
   See application file for complete search history.

(56) References Cited

U.S. PATENT DOCUMENTS

| | | | |
|---|---|---|---|
| 4,672,652 A | 6/1987 | Hiittenrauch et al. | |
| 5,272,760 A * | 12/1993 | Echerer et al. | 382/132 |
| 5,923,724 A * | 7/1999 | Soukal | 378/98.7 |
| 6,263,044 B1 * | 7/2001 | Joosten | 378/98.7 |
| 2007/0274586 A1 * | 11/2007 | Yamano et al. | 382/162 |
| 2009/0238325 A1 | 9/2009 | Kargar et al. | |
| 2009/0238331 A1 | 9/2009 | Kargar et al. | |

* cited by examiner

*Primary Examiner* — Aaron M Richer
*Assistant Examiner* — Nicholas R Wilson
(74) *Attorney, Agent, or Firm* — Peter R. Withstandley

(57) ABSTRACT

A filtered medical image display system includes an interface processor for receiving data. The received data indicates, image characteristics of a first medical image obtained using a medical imaging device and in the absence of an X-ray attenuation filter and imaging device settings. A computation processor uses the image characteristics data and imaging device settings in, computing a change in image display characteristics occurring in a portion of the first medical image in response to filtering a medical imaging beam responsible for producing the portion of the first medical image and determining an adjustment of image display characteristics of the first medical image by scaling image display characteristics of the first medical image including the filtered portion. A display processor uses the determined adjustment in the image display characteristics of the first medical image to generate data representing a second medical image.

15 Claims, 10 Drawing Sheets

SYSTEM FOR MEDICAL IMAGE DISPLAY AND IMAGE FILTER SELECTION

This is a non-provisional application of provisional application Ser. No. 61/184,354 filed Jun. 5, 2009, by R.S. Sipiorski.

FIELD OF THE INVENTION

This invention concerns a filtered medical image display system for predicting change in display characteristics occurring in a portion of a medical image in response to introduction of an X-ray attenuation filter selected by a user for filtering a medical imaging beam associated with providing the portion of the medical image.

BACKGROUND OF THE INVENTION

A known system enables a User to position X-ray collimator blades and X-ray attenuation filters over regions of patient anatomy based on a captured anatomical image frame. In known systems, image graphics used to guide collimator blade repositioning typically utilize a white border outlining an X-ray attenuation filter profile. Additionally, some primitive symbols (such as simple triangles) are placed inside the graphics representing an X-ray attenuation filter as shown in FIG. 1. The image graphics indicate to a user a collimator blade position when radiation is subsequently applied. A real X-ray attenuation filter reduces the image brightness within the X-ray attenuation filter boundaries and brightens the area outside the X-ray attenuation filter boundaries. However; known systems fail to give a user a substantially accurate indication of what X-ray image will be produced using a repositioned collimator blade configuration when X-rays, for example, are applied. A system according to invention principles addresses these deficiencies and related problems.

SUMMARY OF THE INVENTION

A system overlays an X-ray image with semi-transparent Graphical elements representing an X-ray attenuation filter and simulates use of X-ray attenuation filter without requiring additional radiation exposure enabling a physician to more accurately position X-Ray collimator filters. In contrast, known systems fail to digitally filter an image impression within the boundaries of a graphic outline, and they fail to change the image impression outside the filtered area. A filtered medical image display system includes an interface processor for receiving data. The received data indicates, image characteristics of a first medical image obtained using a medical imaging device and in the absence of an X-ray attenuation filter and imaging device settings. A computation processor uses the image characteristics data and imaging device settings in, computing a change in image display characteristics occurring in a portion of the first medical image in response to filtering a medical imaging beam responsible for producing the portion of the first medical image and determining an adjustment of image display characteristics of the first medical image by scaling image display characteristics of the first medical image including the filtered portion. A display processor uses the determined adjustment in the image display characteristics of the first medical image to generate data representing a second medical image.

DETAILED DESCRIPTION OF THE INVENTION

A system overlays an X-ray image with semi-transparent Graphical elements representing an X-ray attenuation filter and simulates use of an X-ray attenuation filter enabling a physician to more accurately position X-Ray collimator filters. The system presents a clinician with semi-transparent graphical elements indicating X-ray attenuation filter position and simulates associated filtering of an X-ray image to enable a clinician to more accurately position X-ray attenuation filters before X-rays are applied to the patient. This reduces the need for repositioning of X-ray attenuation filters and subjecting a patient to redundant radiation exposure. The system accurately displays to a physician and Radiotherapy system operator what an actual image impression will be before x-rays are applied to the patient, preventing un-necessary X-ray radiation exposure of the patient associated with final positioning of the X-ray attenuation filter. The system overlays an X-ray image with semi-transparent graphical elements identifying an X-ray attenuation filtered region enabling a physician to more accurately position X-ray attenuation filters before X-ray radiation is applied to the patient and reducing the need for repositioning X-Ray collimator filters during superfluous radiation exposure of the patient.

Figure 1:
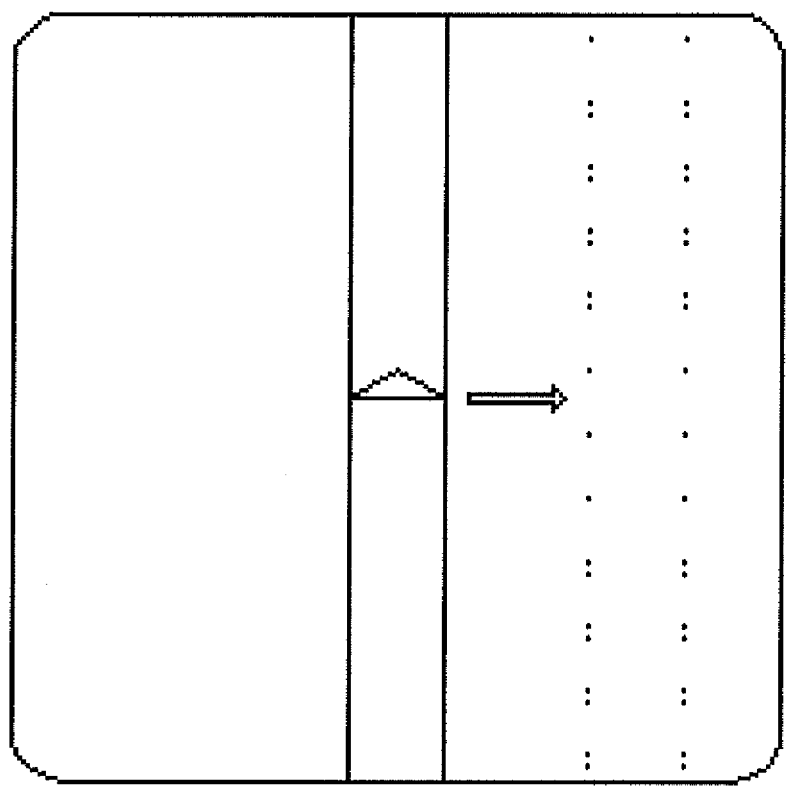
FIG. 1 illustrates a display image indicating positioning and re-positioning of collimator blades in a known system.
Figure 2:
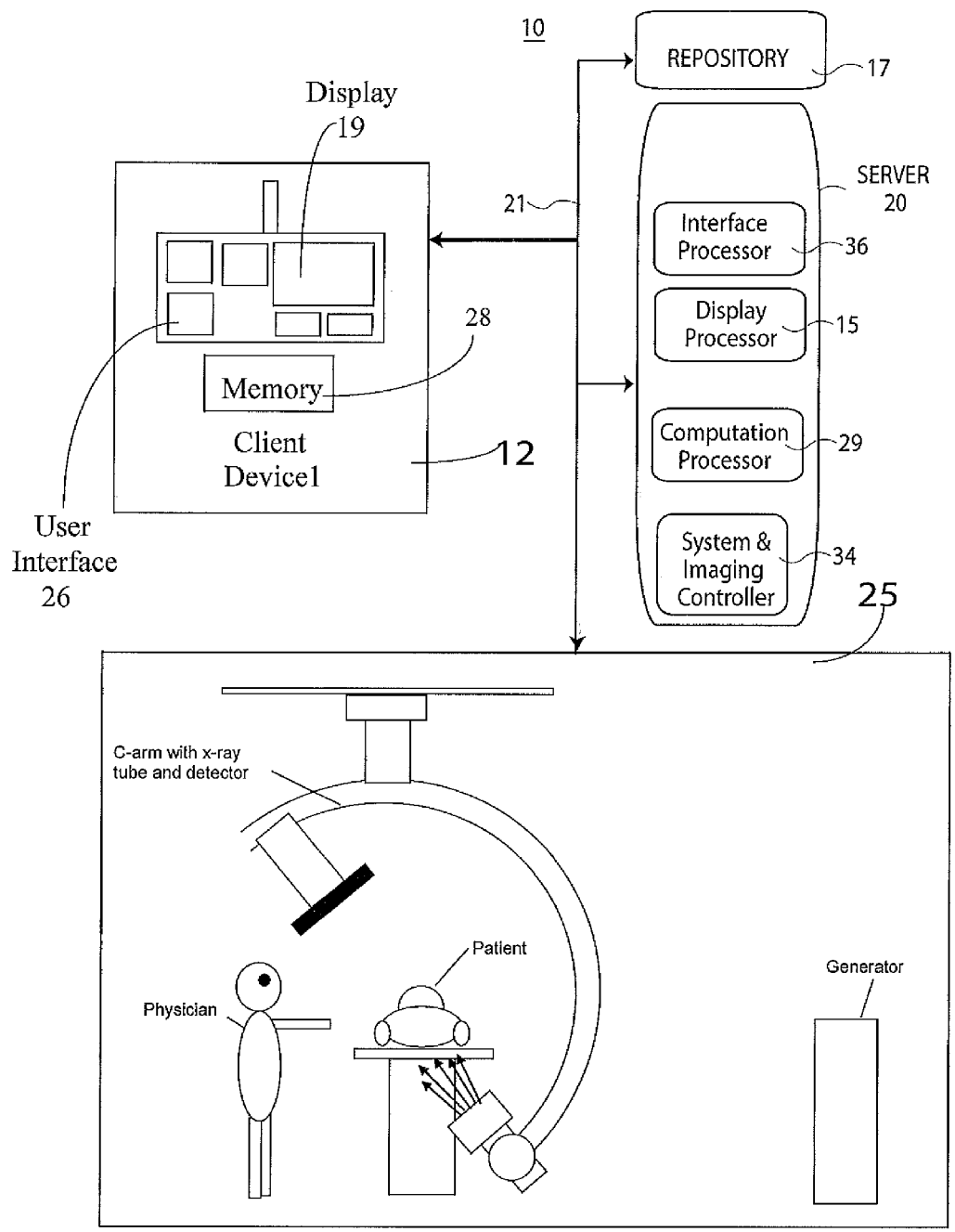
FIG. 2 shows a filtered medical image display system, according to invention principles.

FIG. 2 shows filtered medical image display system 10. System 10 includes one or more processing devices (e.g., computers, workstations or portable devices such as notebooks, Personal Digital Assistants, phones) 12 that individually include display 19, memory 28 and user interface control device 26 such as a keyboard, mouse, touchscreen, voice data entry and interpretation device. System 10 also includes at least one repository 17, X-ray imaging modality system 25 (which in an alternative embodiment may comprise an MR (magnetic resonance), CT scan, or Ultra-sound system, for example) and server 20 intercommunicating with device 12 via network 21. X-ray modality system 25 comprises a C-arm including an X-ray radiation source and detector device, rotating about a patient table and an associated electrical generator for providing electrical power for the X-ray radiation system. The display images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images. Server 20 includes interface processor 36, display processor 15, computation processor 29 and system and imaging controller 34. Display processor 15 provides data representing display images comprising a Graphical User Interface (GUI) for presentation on display 19 of processing device 12. Imaging controller 34 controls operation of imaging device 25 in response to user commands entered via user interface 26. In alternative arrangements, one or more of the units in server 20 may be located in device 12 or in another device connected to network 21.

Interface processor 36 receives data indicating, image characteristics of a first medical image obtained using medical imaging device 25 and in the absence of an X-ray attenuation filter and imaging device settings. Computation processor 29 uses the image characteristics data and imaging device settings in computing a predicted change in display characteristics occurring in a portion of the first medical image in response to introduction of an X-ray attenuation filter selected by a user for filtering a medical imaging beam associated with producing the portion of the first medical image. Display processor 15 uses the computed predicted change in display characteristics in generating data representing the first medical image adjusted to indicate the change in display characteristics occurring in the portion of the medical image.

Figure 3:
FIG. 3 shows a chest X-ray image of a patient.
Figure 4:
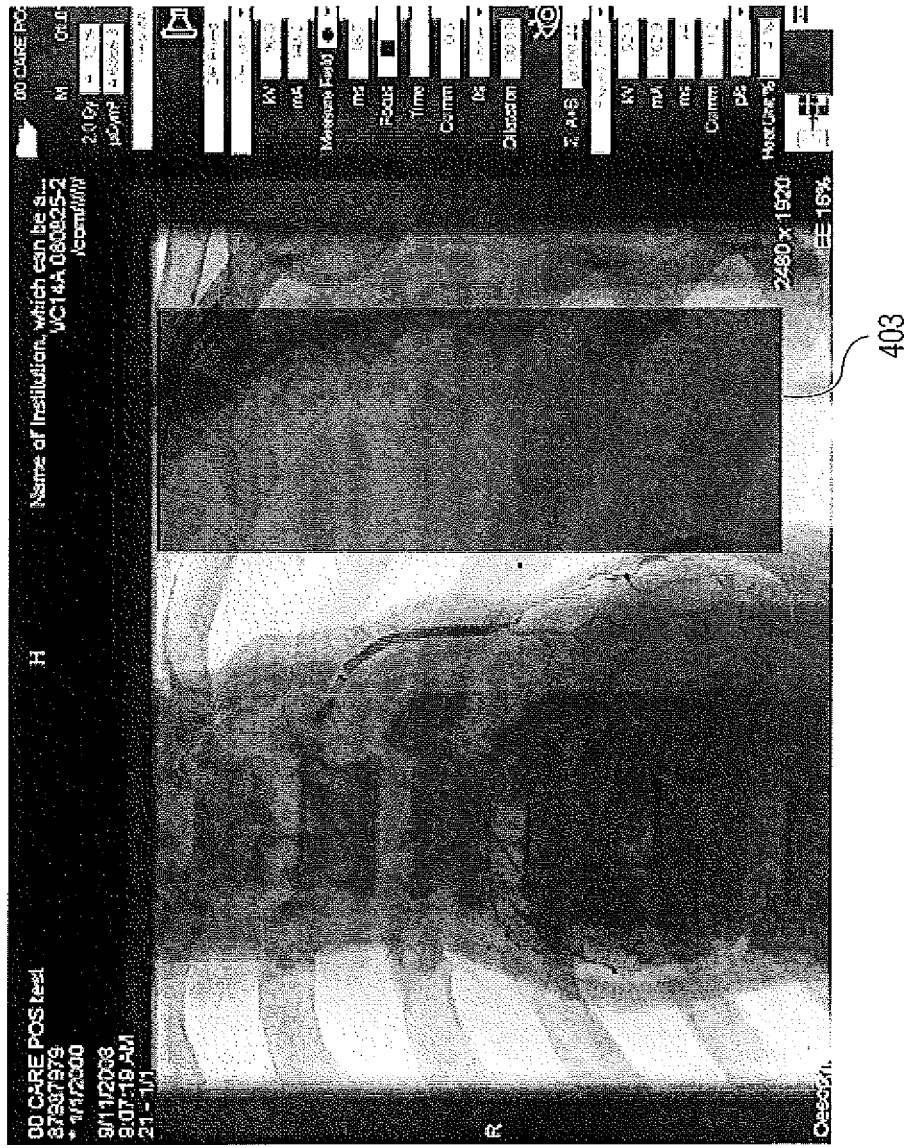
FIG. 4 illustrates mathematical modelling of a semi-transparent filter overlay region, according to invention principles.

FIG. 4 illustrates mathematical modelling of a semi-transparent filter overlay region. Specifically, system 10 advantageously generates data representing a semi-transparent graphical element (rectangle) 403 representing an irradiated region of an image filtered by a collimator filter that is positioned over a relatively bright region of the chest X-ray image of FIG. 3. The filtering within region 403 enables imaging device 25 to acquire an image having enhanced brightness over a region of interest. System 10 (FIG. 2) advantageously provides a user with substantially the same image impression by mathematical modeling and simulation as an actual X-ray attenuation filter will provide under X-ray radiation. Thus a user is able to rotate and move a semi-transparent filter within an X-ray image to simulate positioning of an X-ray attenuation filter. Semi-transparent graphical overlay 403 advantageously gives a user a clearer view of the effect of an X-ray attenuation filter before radiation is applied to the patient by advantageously indicating brightness and contrast inside and outside the filter region.

System 10 selects a semi-transparent graphical overlay region to match an X-ray attenuation filter. System 10 advantageously displays a moveable semi-transparent filter and changes image contrast and brightness to match actual changes which occur to an X-ray image with use of a positioned semi-transparent filter to provide a filtered image region. Thereby, system 10 models changes which would occur to the image with the positioning of the semi-transparent filter. The overall and regional brightness and contrast changes are modeled using multiple input parameters to determine change that occurs to an X-ray image impression. The input parameters include, the acceleration high voltage (KV) and current-time product (mAs) at the high voltage used in X-ray radiation emission, a current X-ray imaging window width ($C_{WW}$) and window center ($C_{WC}$) and a histogram indicating number of pixels having particular luminance intensity levels in a current (Last Image Hold) X-ray image frame, dose sampling field positions in the image frame, Complete Image data (original image with no semi-transparent filter applied) and Composite Image data (original image plus added semi-transparent filter applied. System 10 provides a simulated image substantially matching an image that would be produced using an X-ray attenuation filter in an X-ray image acquisition advantageously reducing patient radiation exposure, since fine adjustments can be implemented with a semi-transparent filter, without applying Radiation to the patient.

Figure 5:
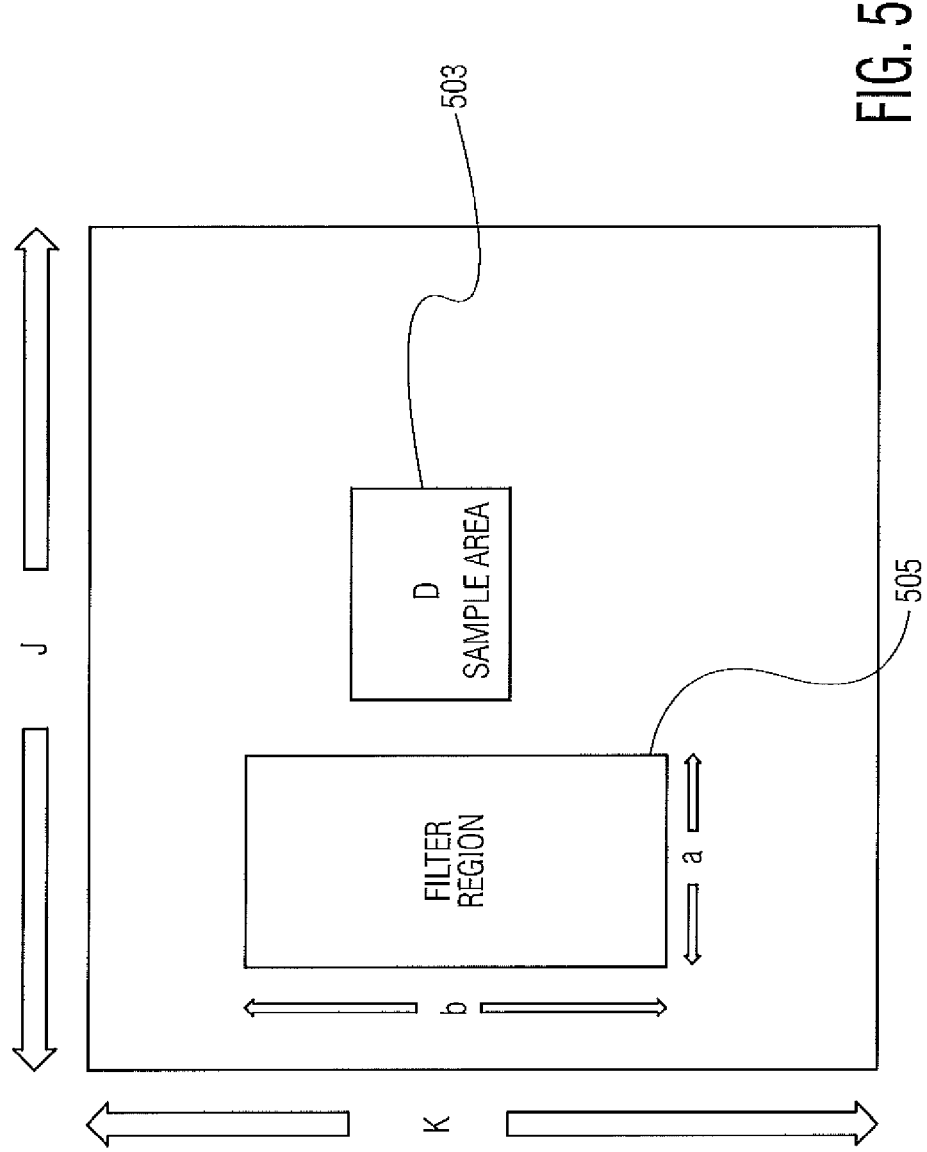
FIG. 5 illustrates mathematical modelling for simulating an X-ray image produced by applying a semi-transparent filter overlay region to an existing X-ray image, according to invention principles.

FIG. 5 illustrates mathematical modelling for simulating an X-ray image produced by applying a semi-transparent filter overlay region 505 to an existing X-ray image. An image is represented by individual pixel luminance values of an image. For the FIG. 5 model, J=image width, K=image Height, C=scaling Factor (comprising weighting KV*mAs*constant), D=sampling area 503, g(a,b)=semi-transparent filter 505 and g(a,b)=0 if b≠k and a≠j.

An image comprises a summation of luminance values of the individual pixels of the image and a Complete Image (original image without filter) is represented by $\Sigma_{K=0,K} \Sigma_{j=0,J} f(j,k)$ and a Composite Image (original image with semi-transparent filter) is represented by $\Sigma_{k=0,K} \Sigma_{j=0,J} f(j,k) g(a,b)$. Further, If (a=D AND b=D) the filter region is in Sampling area 503. A simulated Composite Image is generated by scaling brightness of an image incorporating a filtered region and is represented by, $$\text{Composite Image} = \Sigma_{k=0,K} \Sigma_{j=0,J} f(j,k) \cdot g(a,b) + C$$

This if filter 505 is placed by a user in Sampling Area D 503, system 10 (FIG. 2) scales brightness of an existing image (with brightness subtracted in filter region 505) causing the entire image impression to increase in brightness by scaling Factor C, this yields data representing an equivalent Pre-Exposed image and data representing a Post Exposed Image, giving a physician a final image impression before applying X-ray radiation to a patient.

Figure 6:
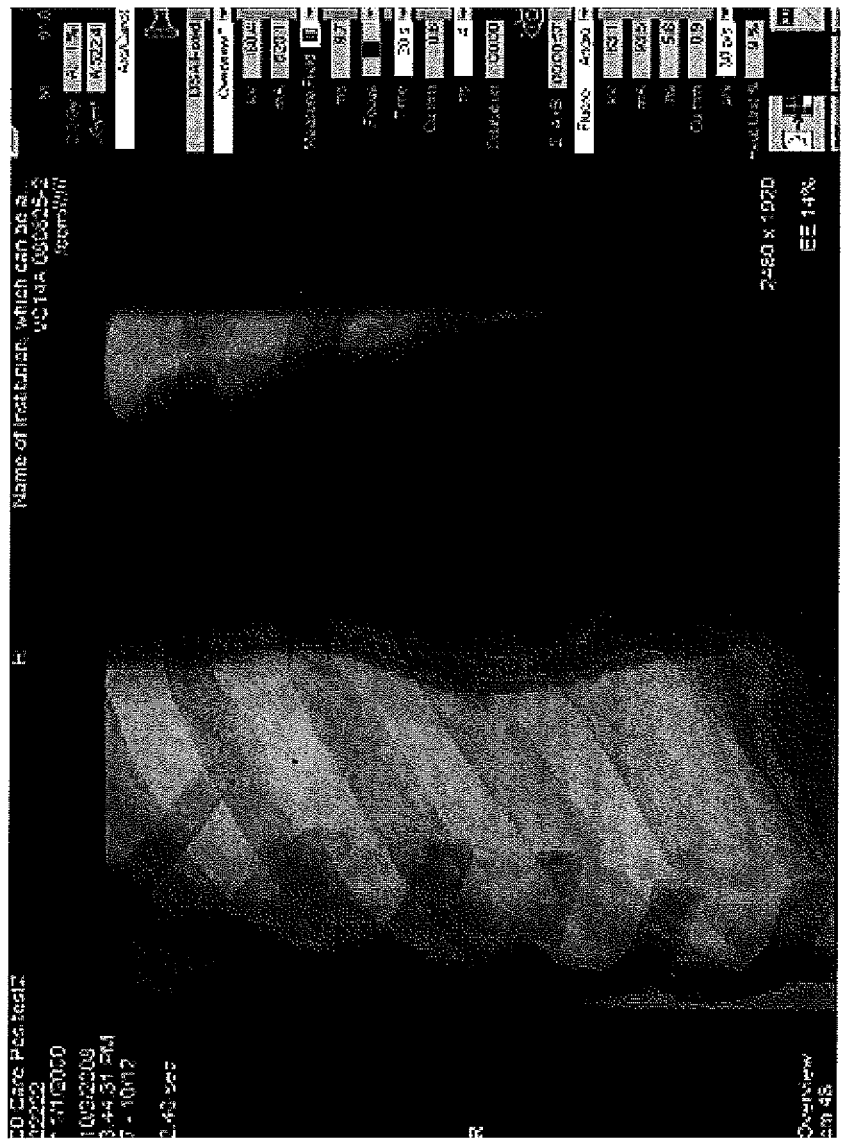
FIGS. 6 and 7 illustrate an original chest X-ray image and a corresponding image with enhanced brightness of the region of interest respectively, with the enhanced brightness image being provided by modeling use of an X-ray attenuation filter, according to invention principles.
Figure 7:
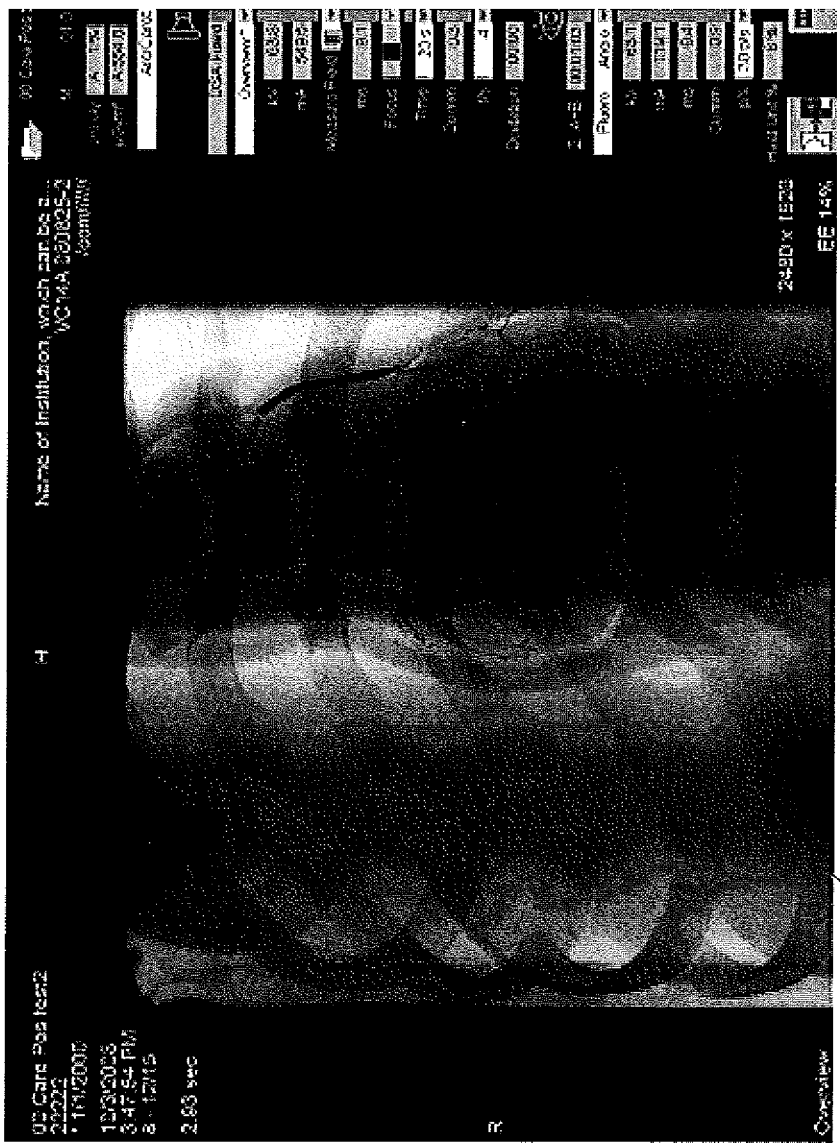

FIG. 6 shows an original chest X-ray image. A user selects and positions a semi-transparent filter region within the FIG. 6 image and system 10 generates data representing a corresponding image FIG. 7 with enhanced brightness of a region of interest by modeling use of a collimator filter. Region 703 indicates an enhanced brightness spinal region provided by system 10.

Figure 8:
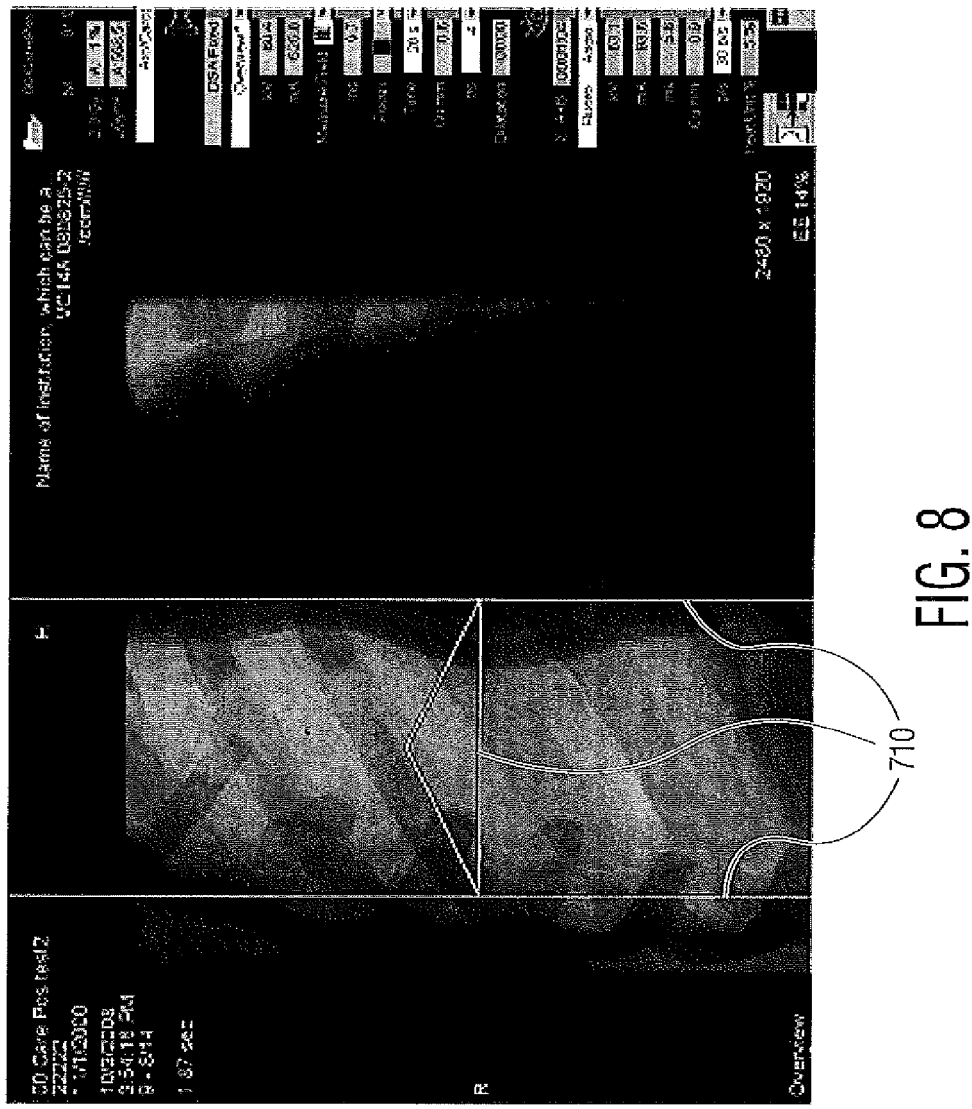
FIG. 8 illustrates a display image indicating graphical elements representing an X-ray attenuation filter region position.
Figure 9:
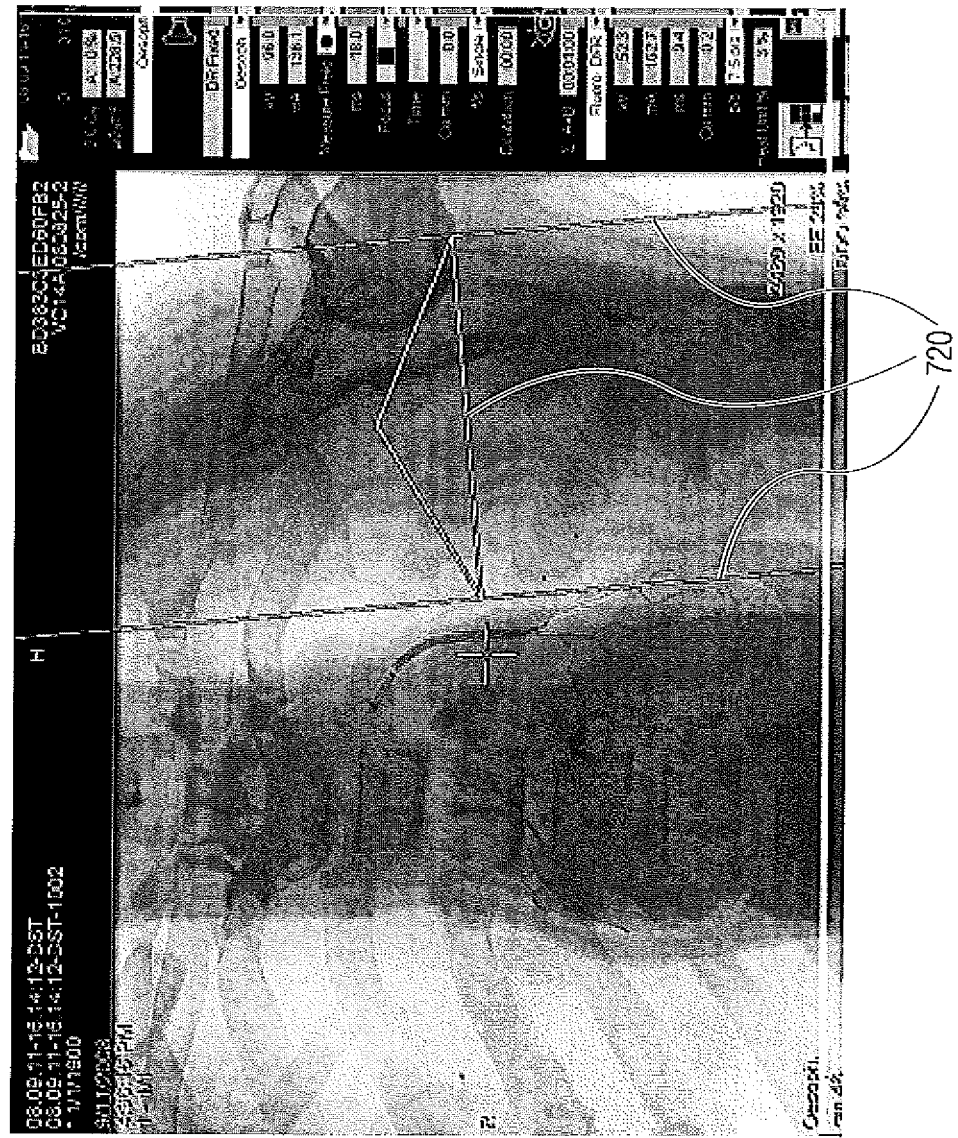
FIG. 9 illustrates a chest X-ray image having enhanced brightness produced using an X-ray attenuation filter positioned as indicated by displayed overlay graphical elements, according to invention principles.

FIG. 8 illustrates a display image indicating graphical elements 710 representing a semi-transparent filter region position that is movable by a user via user interface 26 (FIG. 2). FIG. 9 illustrates a chest X-ray image having enhanced brightness produced using an X-ray attenuation filter positioned as indicated by displayed overlay graphical elements 720.

Figure 10:
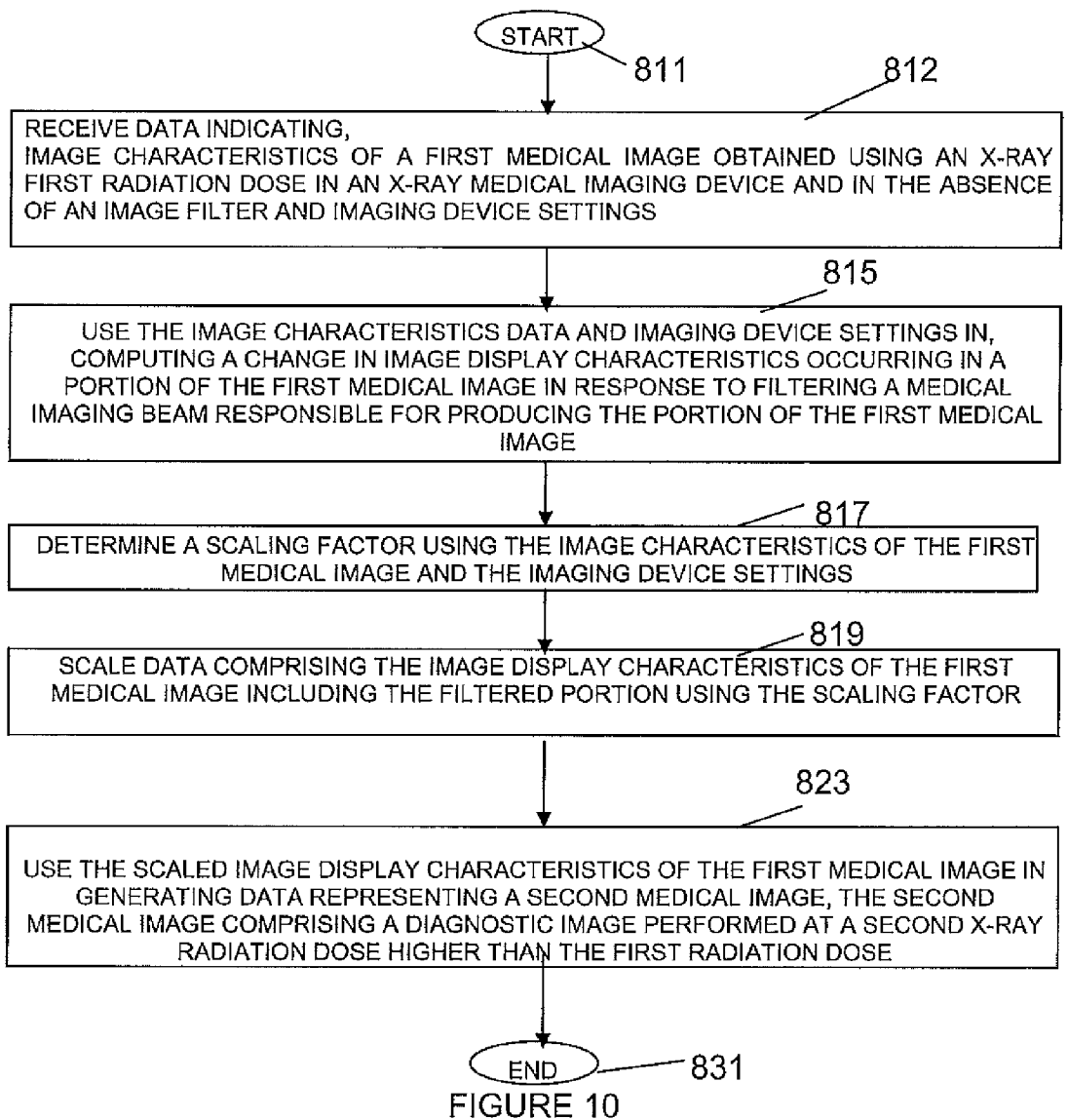
FIG. 10 shows a flowchart of a process used by a filtered medical image display system, according to invention principles.

FIG. 10 shows a flowchart of a process used by digitally filtered medical image display system 10 (FIG. 2) for enhancing visualization of an anatomical region of interest in an X-ray image using X-ray attenuation filters. In step 812 following the start at step 811, interface processor 36 receives data indicating, imaging device settings and image characteristics of a first medical image (a positioning image) obtained using an X-ray first radiation dose in an X-ray medical imaging device (e.g., an X-ray imaging device) and in the absence of an X-ray attenuation filter. The image characteristics of the first medical image include data indicating an image window width, data indicating an image window center and data indicating luminance variation within the first medical image. The imaging device settings include X-ray imaging device settings comprising acceleration X-ray voltage potential and milli-Amp seconds applied in obtaining the first medical image. Interface processor 36 also receives data indicating characteristics including data indicating characteristics of the user selected filter including degree of X-ray attenuation of the user selected X-ray attenuation filter and data substantially indicating the size and location of a portion of the first medical image.

In step 815, computation processor 29 uses the image characteristics data and imaging device settings in, computing a change in image display characteristics occurring in a portion of the first medical image in response to filtering a medical imaging beam responsible for producing the portion of the first medical image. The image display characteristics comprise at least one of, (a) luminance, (b) contrast and (c) brightness. Computation processor 29 in step 817 uses the image characteristics data and imaging device settings in determining an adjustment of image display characteristics of the first medical image by determining a scaling factor and in step 819 scales data comprising the image display characteristics of the first medical image including the X-ray attenuation filtered portion. Computation processor 29 determines the scaling factor using image characteristics including, an X-ray imaging window width, an X-ray imaging window center and a histogram indicating number of pixels having particular luminance intensity levels in an X-ray image frame. Computation processor 29 determines the scaling factor also using imaging device settings including an acceleration high voltage (KV) and milli-amp seconds (mAs) at the high voltage.

In one embodiment, computation processor 29 also uses the image characteristics data and imaging device settings in computing a change in image display characteristics occurring in multiple portions of the first medical image in response to introduction of multiple X-ray attenuation filters selected by a user for filtering a medical imaging beam responsible for producing the multiple portions of the first medical image and in determining the adjustment by scaling image display characteristics of the first medical image including the filtered portions.

In step 823 display processor 15 uses the scaled image display characteristics of the first medical image in generating data representing a second medical image. Specifically, display processor 15 uses the determined adjustment in the image display characteristics of the first medical image in generating data representing the second medical image adjusted to indicate the change in image display characteristics. The process of FIG. 10 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, tinder control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 2-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system generates a simulated Composite Image by subtracting brightness from a filtered region of an image and by scaling brightness of the resultant image incorporating a filtered region according to calculated scaling criteria. Further, the processes and applications may, in alternative embodiments, be located on one or more (e.g., distributed) processing devices on a network linking the units of FIG. 2. Any of the functions and steps provided in FIGS. 2-10 may be implemented in hardware, software or a combination of both.

What is claimed is:

1. A filtered medical image display system, comprising:
   an interface processor for receiving data indicating,
     image characteristics of a first medical image obtained using a medical imaging device and in the absence of an image filter, wherein the first medical image comprises a positioning image obtained using a first X-ray radiation dose, and
     imaging device settings;
   a computation processor for using the image characteristics data and imaging device settings in,
     computing a change in image display characteristics occurring in a filtered portion of said first medical image in response to filtering a medical imaging beam responsible for producing said filtered portion of said first medical image, and determining an adjustment of image display characteristics of said first medical image by scaling image display characteristics of said first medical image including said filtered portion, to increase brightness of said first medical image having brightness subtracted in said filtered portion, in response to the computed change in image display characteristics occurring in said filtered portion in response to said filtering; and a display processor for using the determined adjustment in said image display characteristics of said first medical image in generating data representing a second medical image, wherein the second medical image comprises a diagnostic image obtained using a second X-ray radiation dose higher than the first X-ray radiation dose.

2. A system according to claim 1, wherein
said computation processor scales image display characteristics comprising at least one of contrast and luminance to adjust brightness of the first medical image including both filtered and unfiltered portions,
said interface processor receives data indicating characteristics of a user selected X-ray attenuation filter including data indicating the size and location of said filtered portion of said medical image, and
said computation processor uses the received data indicating characteristics of the user selected X-ray attenuation filter in computing said change in image display characteristics occurring in said filtered portion of said first medical image and scales brightness of said first medical image by a scaling factor to provide simulated image data for use as said second image.

3. A system according to claim 2, wherein
said characteristics of the user selected X-ray attenuation filter comprise data indicating degree of X-ray attenuation.

4. A system according to claim 1, wherein said filtered portion of the first medical image is movable by a user via a user interface control device.

5. A system according to claim 1, wherein
said image display characteristics comprise at least one of, (a) luminance, (b) contrast and (c) brightness and
said computation processor determines a scaling factor using said image characteristics of said first medical image and said imaging device settings and scales data comprising said image display characteristics using said scaling factor.

6. A system according to claim 1, wherein
said computation processor uses the image characteristics data and imaging device settings in computing a change in image display characteristics occurring in a plurality of filtered portions of said first medical image in response to introduction of a plurality of X-ray attenuation filters selected by a user for filtering a medical imaging beam responsible for producing said plurality of filtered portions of said first medical image and in determining said adjustment by scaling image display characteristics of said first medical image including said plurality of filtered portions.

7. A system according to claim 1, wherein
said image characteristics of said first medical image include at least one of, (a) data indicating an image window width, (b) data indicating an image window center and (c) data indicating luminance variation within said first medical image.

8. A system according to claim 1, wherein
said imaging device settings include X-ray imaging device settings comprising at least one of, (a) acceleration X-ray voltage potential and (b) milli-Amp seconds applied in obtaining said first medical image.

9. A filtered medical image display system, comprising:
an interface processor for receiving data indicating,
image characteristics of a first medical image obtained using an X-ray first radiation dose in an X-ray medical imaging device and in the absence of an X-ray attenuation filter, wherein the first medical image comprises a positioning image obtained using the first X-ray radiation dose, and
imaging device settings;
a computation processor for using the image characteristics data and imaging device settings in,
computing a change in image display characteristics occurring in a filtered portion of said first medical image in response to filtering a medical imaging beam responsible for producing said filtered portion of said first medical image, and
scaling image display characteristics of said first medical image including the filtered portion, to increase brightness of said first medical image having brightness subtracted in said filtered portion, in response to the computed change in image display characteristics occurring in said filtered portion in response to said filtering; and
a display processor for using the scaled image display characteristics of said first medical image in generating data representing a second medical image, said second medical image comprising a diagnostic image obtained using a second X-ray radiation dose higher than said first X-ray radiation dose.

10. A system according to claim 9, wherein
said computation processor scales said image display characteristics comprising at least one of, (a) luminance, and (b) contrast to adjust brightness of said first medical image including both filtered and unfiltered portions and
said computation processor determines a scaling factor using said image characteristics of said first medical image and said imaging device settings and scales data comprising said image display characteristics using said scaling factor to provide simulated image data for use as said second image.

11. A system according to claim 10, wherein
said computation processor determines said scaling factor using image characteristics of said first medical image and imaging device settings, said image characteristics include at least one of, (a) an X-ray imaging window width, (b) an X- ray imaging window center and (c) a histogram indicating number of pixels having particular luminance intensity levels in an X-ray image frame, said imaging device settings include at least one of, (i) an acceleration high voltage (KV) and (ii) current (mAs) at the high voltage.

12. A system according to claim 9, wherein
said interface processor receives data indicating characteristics of the user selected filter including data indicating the size and location of said filtered portion of said medical image, and
said computation processor uses the received data indicating characteristics of the user selected filter in computing said change in image display characteristics occurring in said filtered portion of said first medical image.

13. A system according to claim 12, wherein
said characteristics of the user selected filter comprise data indicating degree of X-ray attenuation.

14. A method for providing a filtered medical image for display, comprising the activities of:
receiving data indicating,
image characteristics of a first medical image obtained using an X-ray first radiation dose in an X-ray medical imaging device and in the absence of an image filter; and
imaging device settings;
using the image characteristics data and imaging device settings in,
computing a change in image display characteristics occurring in a filtered portion of said first medical image in response to filtering a medical imaging beam responsible for producing said filtered portion of said first medical image, and
scaling image display characteristics of said first medical image including the filtered portion, to increase brightness of said first medical image having brightness subtracted in said filtered portion, in response to the computed change in image display characteristics occurring in said filtered portion in response to said filtering; and
using the scaled image display characteristics of said first medical image in generating data representing a second medical image, said second medical image comprising a diagnostic image obtained using a second X-ray radiation dose higher than said first X-ray radiation dose.

15. A method according to claim 14, wherein said computation processor scales said image display characteristics comprising at least one of, (a) luminance, and (b) contrast to adjust brightness of said first medical image including both filtered and unfiltered portions and including the activities of
determining a scaling factor using said image characteristics of said first medical image and said imaging device settings and
scaling data comprising said image display characteristics using said scaling factor by scaling luminance or contrast of said first medical image by said scaling factor to provide simulated image data for use as said second image.

* * * * *